United States Patent [19]

Forbus et al.

[11] 4,449,961

[45] May 22, 1984

[54] PROCESS FOR LIGHT OLEFIN PRODUCTION

[75] Inventors: Nancy P. Forbus, Newtown, Pa.; Margaret M. Wu, Belle Mead, N.J.

[73] Assignee: Mobil Oil Corporation, New York, N.Y.

[21] Appl. No.: 474,842

[22] Filed: Mar. 14, 1983

Related U.S. Application Data

[63] Continuation-in-part of Ser. No. 449,912, Dec. 15, 1982, abandoned, which is a continuation-in-part of Ser. No. 335,796, Dec. 30, 1981, abandoned.

[51] Int. Cl.$^3$ .............................................. C07C 1/20
[52] U.S. Cl. ................................. 585/640; 585/408; 585/469; 585/733
[58] Field of Search ............... 585/408, 469, 639, 640, 585/733; 252/455 Z

[56] References Cited

U.S. PATENT DOCUMENTS

| | | | |
|---|---|---|---|
| 4,062,905 | 12/1977 | Chang et al. | 585/640 |
| 4,079,095 | 3/1978 | Givens et al. | 585/640 |
| 4,079,096 | 3/1978 | Givens et al. | 585/640 |
| 4,229,608 | 10/1980 | Chen et al. | 585/640 |
| 4,393,265 | 7/1983 | Bonifaz | 585/639 |

FOREIGN PATENT DOCUMENTS 0009894   4/1980   European Pat. Off. .

*Primary Examiner*—Delbert E. Gantz
*Assistant Examiner*—A. Pal
*Attorney, Agent, or Firm*—A. J. McKillop; M. G. Gilman; E. F. Kenehan, Jr.

[57] ABSTRACT

A process for converting methanol and/or methyl ether to light olefins over a zeolite catalyst comprising at least some crystalline aluminosilicate zeolitic material having pore windows formed by 8-membered rings of oxygen atoms, e.g., Zeolon 500 or ZSM-34, in the presence of hydrogen, or mixtures of hydrogen and carbon monoxide as a gaseous diluent, at elevated temperature and pressure. By using such zeolite catalysts, hydrogen-containing diluents and reaction conditions, methanol and/or methyl ether can be converted to an olefin-containing hydrocarbon product enriched in ethylene and propylene with enhanced catalyst lifetime.

20 Claims, No Drawings

PROCESS FOR LIGHT OLEFIN PRODUCTION

CROSS-REFERENCE TO RELATED APPLICATION

This application is a continuation-in-part of the copending application of Nancy P. Forbus and Margaret May-Som Wu, said application having Ser. No. 449,912, filed Dec. 15, 1982, now abandoned which is, in turn, a continuation-in-part of the then-copending application of Nancy P. Forbus and Margaret May-Som Wu, Ser. No. 335,796, filed Dec. 30, 1981, now abandoned.

BACKGROUND OF THE INVENTION

1. Field of the Invention

This invention relates to an improved process for converting methanol and/or methyl ether to light olefins over crystalline aluminosilicate zeolite catalysts.

2. Description of the Prior Art

A remarkable growth in the production of synthetic fibers, plastics and rubber has taken place in recent decades. Such growth, to a large extent, has been supported and encouraged by an expanding supply of inexpensive petroleum raw materials such as ethylene and propylene. However, increasing demand for these light olefins has, from time to time, led to periods of shortage, either due to a diminished supply of suitable feedstocks or to limited processing capacity. In any event, it is now considered highly desirable to provide efficient means for converting raw materials other than petroleum to light olefins.

One such non-petroleum source of light olefins is coal-derived methanol and methyl ether. In this respect, it is known that methanol or methyl ether can be catalytically converted to olefin-containing hydrocarbon mixtures by contact under certain conditions with particular types of crystalline zeolite catalyst materials. U.S. Pat. No. 4,025,575, issued May 24, 1977, to Chang et al and U.S. Pat. No. 4,083,889, issued to Apr. 11, 1978 to Caesar et al, for example, both disclose processes whereby methanol and/or methyl ether can be converted to an olefin-containing product over a ZSM-5 type (constraint index 1–12) zeolite catalyst. ZSM-5, in fact, converts methanol and/or methyl ether to hydrocarbons containing a relatively high concentration of light ($C_2$ and $C_3$) olefins with prolonged catalyst lifetime before catalyst regeneration becomes necessary.

It is also known that other types of zeolite catalysts can be used to convert methanol and/or methyl ether to olefin-containing hydrocarbon products containing even higher proportions of light olefins than can be realized by methanol/methyl ether conversion over ZSM-5. For example, U.S. Pat. Nos. 4,079,095 and 4,079,096, both issued Mar. 14, 1978, to Givens, Plank and Rosinski, disclose that zeolites of the erionite-offretite type, and especially ZSM-34, can usefully be employed to promote conversion of methanol and/or methyl ether to products comprising a major amount of $C_2$ and $C_3$ light olefins. U.S. Pat. Nos. 4,062,905, issued Dec. 13, 1977 to Chang, Lang and Silvestri, discloses similar methanol conversion processes over small pore zeolites such as erionite, chabazite, Zeolite T and Zeolite ZK-5. However, while erionite-offretite type catalysts are highly selective to light olefins production, such smaller pore zeolites tend to age rapidly in comparison to ZSM-5 when used for methanol/methyl ether conversion. There is thus a continuing need to develop new catalytic procedures suitable for selectively converting an organic charge comprising methanol and/or methyl ether to light olefin products with both light olefin selectivity and enhanced catalyst lifetime.

Accordingly, it is an object of the present invention to provide an improved process for converting methanol and/or methyl ether to olefin-containing products with high selectivity to production of light olefins.

It is a further object of the present invention to provide such a selective process wherein catalyst lifetime is enhanced for methanol/methyl ether conversion.

It is a further object of the present invention to provide such a methanol/methyl ether conversion process employing known catalysts, readily available reactants and diluents and commercially practical reaction conditions.

SUMMARY OF THE INVENTION

In accordance with the present invention, a process is provided for the selective conversion of the organic reactants methanol and/or methyl ether to light olefins with enhanced catalyst lifetime. The catalyst employed in such a process comprises at least some crystalline aluminosilicate zeolite material characterized by a crystalline structure having pore windows formed by 8-membered rings of oxygen atoms, e.g., offretite, erionite, chabazite, chabazite-erionite combinations (Zeolon 500), Zeolite T, Zeolite W and ZSM-34. Conversion over such a catalyst occurs in the presence of a gaseous diluent comprising a hydrogen-containing gas such as hydrogen or synthesis gas containing hydrogen and carbon monoxide. Conditions in the conversion reaction zone include a temperature of from about 200° C. to 500° C., a pressure of from about 50 psig to 500 psig, a WHSV for the organic reactants of from about 0.05 to 30 and WHSV for the gaseous diluent of from about 0.003 to 20.

DETAILED DESCRIPTION OF THE INVENTION

Methanol and/or methyl ether can be converted to hydrocarbons in accordance with the present invention by contacting such reactants with a particular type of crystalline aluminosilicate zeolite catalyst material. Such zeolites have a crystal structure that provides constrained access to, and egress from, the intracrystalline free space by virtue of having a pore dimension which is usually greater than about 3.6×3.7 Angstroms. Such zeolites also generally have a Constraint Index substantially greater than 12. Zeolitic material of this type has pore windows of about the size such as would be provided by 8-membered rings of oxygen atoms. It is to be understood that these rings are those formed by the regular disposition of the tetrahedra making up the anionic framework of the crystalline aluminosilicate zeolite, the oxygen atoms themselves being bonded to silicon (or aluminum) atoms at the centers of the tetrahedra.

It should also be understood that the zeolites useful herein include zeolite types which may contain some crystalline zeolitic material having pore windows of a size formed by oxygen atom rings containing more than 8 members. For example, a number of natural and synthetic zeolites are known to comprise intergrowths of more than one type of crystalline material. Thus, a given zeolite may contain some crystalline material which has pore windows formed by 8-membered rings of oxygen atoms and some material having pore windows formed by 10 or 12 membered rings. The zeolites employed in the process of the instant invention are those which have at least a portion of their total crystalline zeolitic material composed of zeolite material having pore windows formed by 8-membered rings of oxygen atoms.

Zeolites which comprise at least some of the 8-membered ring crystalline zeolite material include those of the erionite-offretite family such as synthetic and natural erionite, synthetic and natural offretite, chabazite-erionite combinations, Zeolite T, Zeolite W, natural and synthetic chabazite and ZSM-34. Chabazite, erionite and offretite are all more particularly described in Meier and Olson, *Atlas of Zeolite Structure Types*, published in 1978 by the International Zeolite Association and the references cited therein. Zeolite T is described in U.S. Pat. No. 2,950,952 and Zeolite W is described in U.S. Pat. No. 3,012,853. All of these publications and patents are incorporated herein by reference.

A naturally occurring zeolite which is a combination of chabazite and erionite is marketed under the tradename Zeolon 500. The chabazite component of Zeolon 500 has the chemical composition $Ca_2(Al_2Si_8O_{21}) \cdot 13 H_2O$; the erionite component of Zeolon 500 has the chemical composition $(CaMgNa_2K_2)_{4.5}Al_9Si_{27}O_{72} \cdot 27 H_2O$. Zeolon 500 has an effective pore diameter of about 4–5 Angstroms and a theoretical $SiO_2/Al_2O_3$ ratio of from about 4:1 to 6:1.

A particularly preferred zeolite material for use in the catalyst compositions of the present invention is ZSM-34. ZSM-34 and its synthesis are more fully described in Rubin et al; U.S. Pat. No. 4,116,813, issued Sept. 26, 1978 and its parent U.S. Pat. No. 4,086,186, issued Apr. 25, 1978. These patents are also incorporated herein by reference.

ZSM-34 is a unique crystalline aluminosilicate zeolite, belonging to the erionite-offretite family, having the composition, as synthesized, and after drying of:

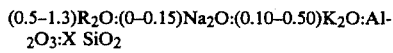

where R is the organic nitrogen-containing cation derived from choline $[(CH_3)_3NCH_2CH_2OH]$ and X is 8 to 50, preferably 8 to 30 and still more preferably 8 to 20. This zeolite, unlike other members of the erionite-offretite family, appears to have a tabular morphology and the capability, after calcination at 1000° F. for at least a period of time to remove the organic cation, of sorbing at least 9.5 weight percent of n-hexane, at ambient temperature and a n-hexane pressure of 20 mm. which is higher than that for any other known offretite or erionite. ZSM-34 is characterized by the X-ray powder diffraction pattern as set forth in the aforementioned U.S. Pat. No. 4,116,813 and U.S. Pat. No. 4,086,186.

All of the foregoing zeolites, as synthesized, may be calcined to remove the organic constituent ($R_2O$) and/or ion exchanged to replace the alkali metal ions with hydrogen ion precursor, e.g. ammonium, and/or other metal ions, particularly metals from Groups IB, IIA, IIB, IIIB, VIIA, VIII and the rare earth metals with only minor changes in the X-ray characterization and sorption properties. The ion exchanged products are catalytically active zeolites useful in the process of this invention.

In practicing the conversion process of the present invention, it may be desirable to incorporate the above-described crystalline aluminosilicate zeolites in another material resistant to the temperature and other conditions employed in the process. Such matrix materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the small pore zeolites employed herein may be compounded with a porous matrix material, such as alumina, silica-alumina, silica-magnesia, silica-zirconia, silica-thoria, silica-beryllia, silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

The process of the instant invention involves utilization of the above-described catalyst compositions to promote the selective conversion of methanol and/or methyl ether to hydrocarbons, particularly light ($C_2$–$C_3$) olefins. Processes of this type are described more fully in U.S. Pat. Nos. 4,079,095; 4,079,096, and 4,062,905, the disclosures of which are incorporated herein by reference.

In accordance with the present invention, a chargestock comprising methanol (methyl alcohol), methyl ether, methanol/methyl ether mixtures or mixtures of such organic reactants with water can be contacted in the vapor phase with the particular catalyst materials hereinbefore described in a reaction zone and under reaction conditions suitable for effecting conversion of methanol and/or methyl ether to olefins. When water is employed along with the organic feed, the amount of water fed with the organic charge of methanol and/or methyl ether can be generally at least about 0.25 moles of water per mole of the organic reactants. Preferably, the amount of water added can be greater than about 0.5 moles of water per mole of organic reactants. The amount of water initially added to the organic charge usually will not exceed about 40 moles per mole of said charge.

In accordance with the present invention, it has been discovered that especially desirable methanol/methyl ether conversion results can be achieved by conducting the conversion reaction under certain selected conditions of temperature and pressure and in the presence of a particular selected gaseous diluent which provides a reducing atmosphere in the conversion reaction zone. The gaseous diluent co-fed to the reaction zone along with the organic reactant(s) to provide such a reducing atmosphere comprises a hydrogen-containing gas which can be selected from hydrogen and mixtures of hydrogen and carbon monoxide such as are found in synthesis gas. The hydrogen-containing gaseous diluent can be co-fed using a weight hourly space velocity (WHSV) of from about 0.003 to 20, preferably from about 0.01 to 10. Generally the molar ratio of hydrogen-containing gaseous diluent to the organic reactants ranges from about 0.5:1 to 40:1, more preferably from about 1:1 to 20:1.

When mixtures of hydrogen and carbon monoxide are used as the gaseous diluent, the molar ratio of hydrogen to carbon monoxide can vary from about 0.2:1 to 10:1, more preferably from about 0.5:1 to 3:1. One source of such hydrogen/carbon monoxide mixtures can comprise synthesis gas from petroleum or coal processing. Synthesis gas for use as the gaseous diluent in the methanol/methyl ether conversion process of this invention consists of a mixture of various gases such as hydrogen, carbon monoxide, carbon dioxide, methane, nitrogen, carbonyl sulfide, carbon disulfide, ammonia, hydrogen sulfide, etc. Such synthesis gas may be derived from fossil fuel conversion by any of the known conversion and gasification methods. The term "fossil fuels", as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood, and cellulosic waste materials also may be used.

Processes for the conversion of coal and other hydrocarbons such as natural gas to a gaseous mixture consisting essentially of hydrogen and carbon monoxide, or of hydrogen and carbon monoxide and carbon dioxide, are well known. Although various processes may be employed for the gasification, those of major importance depend either on the partial combustion of the fuel with an oxygen containing gas or on the high temperature reaction of the fuel with steam, or on a combination of these two reactions. Such gasification processes include in-situ gasification schemes, such as the underground partial combustion of coal and petroleum deposits. An excellent summary of the art of gas manufacture, including synthesis gas useful herein, from solid and liquid fuels, is given in ENCYCLOPEDIA OF CHEMICAL TECHNOLOGY, Edited by Kirk-Othmer, Second Edition, Volumn 10, pages 353–433 (1966), Interscience Publishers, New York, N.Y, the contents of which are herein incorporated by reference.

The raw synthesis gas produced from fossil fuels will contain various impurities such as particulates, sulfur compounds, and metal carbonyl compounds, and will be characterized by a hydrogen-to-carbon oxides ratio which will depend on the fossil fuel and the particular gasification technology utilized. Such raw syngas is generally purified before being used as the gaseous diluent in the methanol/methyl ether conversion process of the present invention.

Whatever the nature of particular hydrogen-containing gaseous diluent utilized, it has been found that gaseous diluents of the type described herein can usefully be employed to prolong the lifetime of the zeolite based methanol/methyl ether conversion catalyst when such catalysts and diluents are employed under particular conditions for the selective conversion of methanol/methyl ether to light olefins. Such conditions include an operating temperature between about 200° C. and 500° C., preferably 300° C. and 450° C., a pressure between about 50 psig (345 kPa) and 500 psig (3447 kPa), preferably about 100 psig (689 kPa) and 250 psig (1724 kPa); and a weight hourly space velocity (WHSV) of the organic reactants of between about 0.05 and 30, preferably 0.1 and 10.

It should be noted that the prior art has recognized that hydrogen can be used as one of several possible diluents for the organic reactants in a zeolite-catalyzed methanol conversion process. The aforementioned U.S. Pat. Nos. 4,079,095; 4,079,096 and 4,062,905, for example, indicate that hydrogen, nitrogen, water, helium and the like can be employed as carrier gases in the disclosed methanol conversion processes. What the prior art has not recognized, however, is that the one particular selected diluent, hydrogen-containing gas, can serve to enhance the lifetime of the particular zeolite catalysts used in a methanol/methyl ether conversion process.

Catalyst lifetime as used herein refers to the length of time on stream during which a given catalyst can be employed before catalytic activity drops to a level such that catalyst regeneration becomes necessary or commercially desirable. A convenient measurement of catalyst lifetime would be the length of time a catalyst can be employed in the process of the present invention before methanol/methyl ether conversion in the process drops from its initial value to below 50%. For purposes of the present invention, enhanced catalyst lifetime refers to the extension of this period of over 50% methanol/methyl ether conversion which occurs when a hydrogen-containing diluent is used in comparison with prior art processes wherein either no diluent is employed or wherein a hydrogen free gas such as water, nitrogen or helium is used as a diluent.

The methanol and/or methyl ether conversion process described herein may be carried out as a batch-type, semi-continuous or continuous operation utilizing a fixed, fluidized or moving bed catalyst system. A preferred embodiment entails use of a catalyst zone wherein the alcohol or ether charge together with gaseous diluent and optionally with added water is passed concurrently or countercurrently through a fluidized or moving bed of particle-form catalyst. The latter after use may be conducted to a regeneration zone wherein the aged catalyst can be regenerated by appropriate regeneration procedures. In a preferred regeneration method, aged catalyst can be contacted with hydrogen-containing gas under elevated temperature and pressure conditions. Such a hydrogen regeneration procedure is more fully described in the copending U.S. patent application of Forbus and Wu, having Ser. No. 335,979, filed Dec. 30, 1981. After regeneration, the regenerated catalyst can be recycled to the conversion zone for further contact with the methanol and/or ether containing feed.

The product stream in the process of the present invention contains steam and a hydrocarbon mixture of paraffins and olefins, which mixture can be substantially devoid of aromatics. This mixture is particularly rich in light olefins, i.e., ethylene and propylene. Generally, a major fraction of the total olefins is ethylene plus propylene with the ethylene content of the product exceeding the propylene content. Thus, the predominant hydrocarbon product constitutes valuable petrochemicals. The steam and hydrocarbon products may be separated from one another by methods well known in the art. In a preferred embodiment of the invention, the unconverted methanol and/or methyl ether, as well as at least part of the water in the product, can be recycled to the reaction zone.

The following examples will serve to illustrate the process of this invention without limiting the same.

EXAMPLE I

ZSM-34 is prepared by interacting the following solutions:

A. Caustic Aluminate 68.89 grams sodium aluminate (20 wt. % Na, 43.1 wt. % $Al_2O_3$, Balance $H_2O$)
29.28 grams NaOH (77.5 wt. % $Na_2O$)
26.4 grams KOH 86.4% KOH
540 grams $H_2O$ B. Silica Solution 780 grams Colloidal Silica sol (30 Wt. % $SiO_2$)

C. Choline Chloride 228 grams

These are mixed together in a 2 liter autoclave adding solution C to solution A and then adding solution B followed by a 15 minute continuous mixing. The autoclave is then sealed, pressure-tested and then heated to and held at 300° F. for 8 days. The contents are stirred continuously during the 8 day crystallization period.

The autoclave and its contents are cooled to room temperature, and the crystalline product is filtered and washed. On analysis the product is found to contain:
Na, wt %: 0.68
K, wt %: 3.59
$Al_2O_3$ wt %: 13.5
$SiO_2$, wt %: 78.5
N, wt %: 2.5

The resulting ZSM-34 product has the following molar composition:

$0.54R_2O:0.11Na_2O:0.35K_2O:Al_2O_3:9.87SiO_2$

A sample of the calcined alkali ZSM-34 is further processed by contacting with a 10 wt % $NH_4Cl$ solution for 1 hour at about 185° F. using 10 ml. of solution for each gram of ZSM-34. A total of four contacts are made at these conditions followed by final filtration and water washing essentially free of chloride ion.

The product is dried at 230° F. and calcined for 10 hours at 1000° F. The residual alkali content as Na is 0.035 wt. % while the residual K content is 1.47 wt. %. This product has a surface area of 517 m²/g and the following sorption capacity:
Cyclohexane, wt %: 2.6
n-Hexane, wt %: 10.0
$H_2O$, wt %: 18.7

EXAMPLE II

ZSM-34 prepared in a manner similar to that of Example I and back-exchanged with ammonium chloride to convert it to the ammonium form is used to convert methanol to hydrocarbons in known manner. The ZSM-34 used in such conversion as a surface area of 475 m²/g and the following sorption capacity:
Cyclohexane, wt. %: 4.5
n-Hexane, wt. %: 9.9
$H_2O$, wt. %: 16.5

In such a procedure, two grams of zeolite (no binder) and four grams of quartz chips, both of 14/20 mesh size, are mixed and packed into a quartz microreactor, equipped with thermocouple. Several cycles are run, and the catalyst is always calcined at 500° C. with air for at least 16 hours before each new cycle. The standard feed contains 37.2% MeOH and 62.8% $H_2O$ (by weight). The methanol/water mixture is fed to the reactor maintained at 370° C./1 atmosphere using a weight hourly space velocity (WHSV) of 4.1. The total reactor effluent is analyzed, on line, by a "n-octane on Poracil" column. Methanol conversion is calculated based on hydrocarbon formation only. Selectivities (wt %) to hydrocarbon product are calculated on "coke free" basis.

The lifetimes for converting 50% of the methanol for each cycle and the corresponding selectivities to $C_2H_4$, $C_3H_6$ and $C_4H_8$ are summarized in Table I.

TABLE I

Catalyst Lifetimes and Selectivities to $C_2H_4$, $C_3H_6$ and $C_4H_8$ by $NH_4ZSM-34$ at 50% MeOH Conversion

| Cycle # | 1 | 2 | 3 | 4 |
|---|---|---|---|---|
| Lifetime for 50% MeOH Conversion, (hours) | 2.6 | 2.0 | 1.7 | 1.4 |
| Selectivities (wt %) at 50% MeOH Conversion | | | | |
| $C_2H_4$ | 61 | 56 | 58 | 55 |
| $C_3H_6$ | 25 | 26 | 29 | 28 |
| $C_4H_8$ | 4 | 7 | 7 | 7 |
| Total $C_2^=-C_4^=$ | 90 | 89 | 94 | 90 |

The Table I data demonstrate that $NH_4ZSM-34$ provides relatively high selectivity to light olefins for conversion of a methanol/water feed to hydrocarbons. Such data also indicate that catalyst lifetime for methanol conversion over $NH_4ZSM-34$ is relatively short.

EXAMPLE III

Another sample of a ZSM-34 zeolite is used to promote conversion of an anhydrous methanol feed to hydrocarbons using the hydrogen co-feed and elevated temperature and pressure conditions of the present invention. In such a procedure, a fresh two gram sample of $NH_4ZSM-34$ in a stainless steel vapor phase reactor fitted with a furnace and both water and dry ice condensers is purged with $H_2$ at 100 cc/min., 350° C. and 125 psig for 6 hours. Methanol is then introduced at 1 cc/hr. The first sample is taken after 24 hours on stream at 350° C. and 125 psig with methanol and hydrogen feeds at WHSV values of 0.4 and 0.2, respectively. The reactor pressure and methanol and hydrogen feed rates are maintained constant throughout the run. For the first 29 hours, when the reactor temperature is 353° C. to 365° C., methanol conversion is below 50%. When the reactor temperature is raised to 375° C., methanol conversion increases to above 65%. The reaction conditions are then maintained constant for 120 hours. The major by-products are $CH_4$, $C_2H_6$ and $C_3H_8$. The run is terminated arbitrarily after a total of 148 hours. The reaction conditions and average results for this run are summarized below:

| | |
|---|---|
| Temperature | 375° C. |
| Pressure | 125 psig |
| WHSV of MeOH | 0.4 |
| WHSV of $H_2$ | 0.2 |
| Methanol Conversion | 75% |
| Selectivity (wt %) | |
| $C_2H_4$ | 55 |
| $C_3H_6$ | 24 |
| $CH_4$ | 7 |
| $C_2H_6$ | 7 |

-continued

| | |
|---|---|
| Others | 7 |
| Total $C_2^=-C_4^=$ | 81 |

EXAMPLE IV

Another continuous series of runs employing NH$_4$ZSM-34 zeolite catalyst were carried out in order to convert an anhydrous methanol feed to hydrocarbon product in the same reactor utilized in Example III. Reaction conditions were varied for each run. Except as noted, no regeneration procedures are employed between runs. Reaction conditions, methanol conversion and light olefins selectivity for each run are set forth in Table II.

TABLE II
EFFECT OF REACTION VARIABLES ON METHANOL CONVERSION OVER ZSM-34

| Run No. | 1 | 2 | 3 | 4 | 5 | 6 | 7 | 8 | 9 | 10 | 11 | 12 |
|---|---|---|---|---|---|---|---|---|---|---|---|---|
| Total time on Stream (hrs) | 2 | 24 | 44 | 71 | 91 | 94 | 120 | 184 | 25 | 80 | 125 | 167 |
| Temperature, °C. | 394 | 394 | 380 | 370 | 370 | 365 | 365 | 365 | 370 | 370 | 370 | 370 |
| Pressure, psig | 500 | 250 | 250 | 250 | 250 | 100 | 100 | 100 | 100 | 200 | 150 | 125 |
| WHSV: H$_2$ | 0.2 | 0.2 | 0.2 | 0.2 | 0.1 | 0.1 | 0.2 | 0.2 | 0.2 | 0.2 | 0.2 | 0.2 |
| MeOH | 0.4 | 0.4 | 0.4 | 0.4 | 0.4 | 0.4 | 0.4 | 0.8 | 0.4 | 0.4 | 0.4 | 0.4 |
| MeOH Conversion, %*** | 100 | 100 | 98 | 66 | 54 | 38 | 41 | 21 | 50** | 70 | 61 | 54 |
| Wt % Selectivity | | | | | | | | | | | | |
| C$_2$H$_4$ | 10 | 33** | 28 | 41 | 43 | 57 | 57 | 49 | 58 | 40 | 48 | 50 |
| C$_3$H$_6$ | 13 | 21 | 27 | 24 | 24 | 24 | 24 | 26 | 25 | 25 | 25 | 25 |
| C$_4$H$_8$ | 12.0 | 10 | 0 | 1 | 0 | 0 | 0 | 0 | 0 | 0 | 2 | 4 |
| CH$_4$ | 10.0 | 11 | 7 | 10 | 12 | 7 | 7 | 9 | 7 | 14 | 11 | 10 |
| C$_2$H$_6$ | 18 | —* | 11 | 10 | 10 | 5 | 4 | 4 | 7 | 13 | 10 | 10 |
| C$_3$H$_8$ | 34.0 | 19 | 15 | 10 | 5 | 3 | 1 | 1 | 2 | 8 | 5 | 2 |
| Others | 3 | 6 | 12 | 4 | 6 | 4 | 7 | 11 | 1 | 0 | 0 | 0 |
| Total C$_2$-C$_4$ = | 35.0 | — | 55 | 66 | 67 | 81 | 81 | 75 | 83 | 65 | 75 | 80 |

*$C_2^*$, $C_2$ = were not separated.
**Methanol conversion never reached a steady state under this set of conditions.
***To hydrocarbons The Table II data demonstrate the effect of temperature, hydrogen and methanol flow rates and reactor pressure on methanol conversion and light olefin selectivity. In Runs 2, 3 and 4 of Table II, the reactor temperature is varied from 394° C. to 370° C. at a constant pressure of 250 psig. The methanol conversion decreases from 100% to 66% and selectivities to ethylene and total light olefins are significantly improved at lower temperature.

Comparing Runs 4 and 5, when the hydrogen feed rate is halved, the steady state methanol conversion decreases from 66% to 54% and selectivities to light olefins remain similar. In Run 8, when the methanol feed rate is doubled, compared to Run 7, the methanol conversion drops from 41% to 21%.

In Run 9 to 12, the effect of reactor pressure is demonstrated by maintaining reactor temperature at 370° C. and WHSV of H$_2$ and MeOH at 0.2 and 0.4, respectively. The reactor pressure is varied from 100 to 200 psig. It is important to note that the catalyst maintains good activity and selectivities to C$_2$, C$_3$ olefins over a wide range of reactor pressures.

EXAMPLE V

Another run employing somewhat different reaction conditions from those of Examples III and IV is carried out to convert methanol to hydrocarbons over NH$_4$ZSM-34 zeolite catalyst. In such testing, 10 grams of undiluted zeolite (14/20 mesh) are used in the same reactor as used in Examples III and IV. Both a liquid water phase from the condensers and uncondensed gases are collected and analyzed. The volume of hydrocarbons is determined by substracting the volume of hydrogen feed from the total volume of non-condensed gas obtained. The liquid water phase is analyzed for water, methanol and methyl ether on a ⅛″×3′ Poropak T column. The gases are analyzed on an ⅛″×8′ Silica Gel column (Analabs) 100/120 mesh. Material balances are calculated from the liquid and two gaseous samples analyzed.

The catalyst in the reactor is heated in a flowing hydrogen stream for 1.5 hours at 500° C. before introduction of the methanol reactant. Methanol is then introduced with the hydrogen with the temperature lowered to 300° C. Conversion of methanol then continues for 205 hours in a series of runs with varying temperature, pressure, space velocity and molar H$_2$/methanol feed ratios. Reaction conditions, methanol conversion and product selectivities for such a series of runs is set forth in Tables IIIA and IIIB.

TABLE IIIA
METHANOL TO OLEFINS - ZSM-34 RUNS 1-7

| CONDITIONS | RUN NO. | | | | | | |
|---|---|---|---|---|---|---|---|
| | 1 | 2 | 3 | 4 | 5 | 6 | 7 |
| Temp., °C. | 300 | 350 | 360 | 370 | 370 | 370 | 370 |
| Pressure, psig | 125 | 125 | 125 | 125 | 125 | 125 | 125 |
| WHSV | | | | | | | |
| MeOH | .43 | .43 | .43 | .43 | .72 | .46 | .46 |
| H$_2$ | .26 | .26 | .26 | .26 | .26 | .21 | .12 |
| Mole Ratio | 1/10 | 1/10 | 1/10 | 1/10 | 1/6 | 1/7.5 | 1/4 |
| Time on Stream (hrs) | 1.5 | 11 | 21 | 32 | 44 | 67 | 80 |
| Conversion (%) | 99 | 91 | 89 | 100 | 86 | 90 | 71 |
| Select. to Prods. (%) | | | | | | | |
| C$_2$H$_4$ | 14.8 | 33.5 | 41.7 | 36.6 | 42.1 | 40.2 | 41.9 |
| C$_3$H$_6$ | 15.9 | 25.2 | 28.1 | 31.3 | 29.1 | 29.1 | 29.9 |
| C$_4$H$_8$ | 12.0 | 11.0 | 5.5 | 4.7 | 4.4 | 5.7 | 6.1 |
| Total | 42.7 | 69.7 | 75.3 | 72.6 | 75.6 | 75.0 | 77.9 |
| CH$_4$ | 28.1 | 8.9 | 10.8 | 9.6 | 11.5 | 10.8 | 8.3 |
| C$_2$H$_6$ | 2.4 | 7.4 | 8.3 | 8.9 | 7.1 | 8.1 | 8.1 |
| C$_3$H$_8$ | 17.9 | 8.0 | 4.2 | 5.6 | 3.7 | 4.0 | 2.7 |
| C$_4$H$_{10}$ | 6.4 | 1.9 | .3 | .3 | .2 | .2 | .3 |
| Total | 54.8 | 26.2 | 23.6 | 24.4 | 22.5 | 23.1 | 19.4 |
| CO, CO$_2$, C$_5$+ | 2.5 | 4.1 | 1.1 | 2.7 | 1.9 | 1.9 | 2.7 |

TABLE IIIA-continued

METHANOL TO OLEFINS - ZSM-34
RUNS 1-7

| CONDITIONS | RUN NO. | | | | | | |
|---|---|---|---|---|---|---|---|
| | 1 | 2 | 3 | 4 | 5 | 6 | 7 |
| TOTAL | 100.0 | 100.0 | 100.0 | 100.0 | 100.00 | 100.0 | 100.0 |

TABLE IIIB
METHANOL TO OLEFINS - ZSM-34
RUNS 8-14

| CONDITIONS | RUN NO. | | | | | | |
|---|---|---|---|---|---|---|---|
| | 8 | 9 | 10 | 11 | 12 | 13 | 14 |
| Temp., °C. | 390 | 400 | 400 | 390 | 390 | 380 | 380 |
| Pressure, psig | 125 | 400 | 150 | 150 | 175 | 175 | 200 |
| WHSV | | | | | | | |
| MeOH | .43 | .46 | .44 | .44 | .44 | .44 | .44 |
| $H_2$ | .12 | .13 | .12 | .12 | .12 | .12 | .12 |
| Mole Ratio | 1/4.5 | 1/4.5 | 1/4.3 | 1/4.3 | 1/4.3 | 1/4.3 | 1/4.3 |
| Time on Stream (hrs) | 110 | 134 | 149 | 158 | 168 | 180 | 205 |
| Conversion (%) | 94 | 96 | 100 | 91 | 96 | 83 | 94 |
| Select. to Prods. (%) | | | | | | | |
| $C_2H_4$ | 40.7 | 42.9 | 36.2 | 41.5 | 35.2 | 39.0 | 33.9 |
| $C_3H_6$ | 30.2 | 29.6 | 26.5 | 28.7 | 28.2 | 26.5 | 26.9 |
| $C_4H_8$ | 6.7 | 4.7 | 5.3 | 4.3 | 5.7 | 5.0 | 4.1 |
| Total | 77.6 | 77.2 | 68.0 | 74.5 | 69.1 | 70.5 | 64.9 |
| $CH_4$ | 8.5 | 9.1 | 9.5 | 9.9 | 11/2 | 11.6 | 11.5 |
| $C_2H_6$ | 7.3 | 7.9 | 11.4 | 9.7 | 12.6 | 11.9 | 15.5 |
| $C_3H_8$ | 2.4 | 2.1 | 4.1 | 2.6 | 3.5 | 3.2 | 5.5 |
| $C_4H_{10}$ | .4 | .3 | .7 | .2 | .3 | .3 | .4 |
| Total | 18.6 | 19.4 | 25.7 | 22.4 | 27.6 | 27.0 | 32.9 |
| CO, $CO_2$, $C_5+$ | 3.8 | 3.4 | 6.3 | 3.1 | 3.3 | 2.5 | 2.2 |
| TOTAL | 100.0 | 100.0 | 100.0 | 100.0 | 100.0 | 100.0 | 100.0 |

The Table IIIA and IIIB data demonstrate the beneficial effect on conversion and light olefin selectivity of co-feeding hydrogen with methanol when a ZSM-34 zeolite is used to convert methanol to light olefins at temperature of from 300° C. to 400° C. and pressure of from 125 psig to 200 psig.

EXAMPLE VI

A two gram sample of $NH_4ZSM$-34, diluted with four grams of quartz chips (both of 14/20 mesh), is used to convert methanol to hydrocarbons in the same reactor of Examples III, IV and V. The reactor is pressurized to 500 psig with 1/1 (v/v) $CO/H_2$. The reactor temperature is raised to 395° C. and methanol was fed at 1.0 ml/hr. The $CO/H_2$ feed rate is maintained at 100 cc/min. Results at three different temperatures are given in Table IV.

TABLE IV
METHANOL CONVERSION OVER $NH_4ZSM$-34 UNDER $CO/H_2$ PRESSURE (500 psig)

| Run No. | Temp. (°C.) | Time on Stream (hr) | % $CH_2$ Conv. | Hydrocarbon Product Selectivity | | | | | | |
|---|---|---|---|---|---|---|---|---|---|---|
| | | | | $C_1°$ | $C_2°$ | $C_2=$ | $C_3°$ | $C_3=$ | $C_4$ | Others |
| 1 | 395 | 1.0 | 90 | 5.1 | 6.8 | 34.3 | 27.2 | 26.7 | — | — |
| 2 | 395 | 2.0 | 90 | 6.5 | 9.5 | 41.6 | 8.9 | 33.8 | — | — |
| 3 | 395 | 3.5 | 92.1 | 6.2 | 10.5 | 41.5 | 10.2 | 24.5 | 3.9 | 3.2 |
| 4 | 395 | 19.5 | 98.9 | 7.3 | 11.3 | 35.9 | 8.2 | 24.7 | 2.9 | 9.7 |

The Table IV data demonstrate that, by using an $NH_4ZSM$-34 catalyst and an $CO/H_2$ cofeed, methanol can be effectively converted to hydrocarbons with high selectivity to light olefins even after 19 hours on stream.

EXAMPLE VII

Without any regeneration procedure, the gas feed in the Example IV reaction is changed to pure $H_2$ and the methanol reaction continued. Methanol conversion and product selectivities at 370° C., hydrogen flow of 100 cc/min, $CH_3OH$ feed of 1 ml/hr and various pressures are summarized in Table V.

TABLE V
METHANOL CONVERSION OVER $NH_4ZSM$-34 UNDER $H_2$ PRESSURE

| Pressure (psig) | Time on Stream (hr) | % $CH_2$ Conv. | Hydrocarbon Product Selectivity* | | |
|---|---|---|---|---|---|
| | | | $C_2=$ | $C_3=$ | $C_2=-C_4=$ |
| 100 | 4.5 | 77.1 | 52.7 | 26.5 | 83.0 |
| 100 | 21.9 | 37.3 | 52.3 | 25.5 | 80.4 |
| 200 | 23.5 | 51.4 | 39.8 | 23.1 | 65.6 |
| 150 | 76.4 | 72.5 | 45.7 | 24.3 | 72.5 |
| 125 | 125.4 | 54.2 | 52.8 | 23.4 | 78.4 |
| 125 | 165.2 | 68.4 | 49.8 | 26.0 | 78.3 |

*Balance of the products contains mostly $CH_4$, $C_2H_6$, $C_3H_8$ and $C_4H_{10}$ The Table V data again demonstrate the beneficial effect of an $H_2$ co-feed at elevated pressure on catalyst lifetime when $NH_4ZSM$-34 zeolite is used to promote conversion of methanol to light olefins.

EXAMPLE VIII

A commercially available natural zeolite which is a combination of chabazite and erionite, i.e. Zeolon 500, is prepared for use in a methanol conversion process. A 40 gram sample of Zeolon 500 powder was slurried in an aqueous solution containing 16 gram $NH_4NO_3$ in 200 cc deionized water. The slurry was stirred gently for 16 hours. The zeolite was filtered and washed with 100 cc deionized water. The final product was dried at 100° C. under vacuum for 2 hours. The catalyst was pelletized to 14/20 mesh.

EXAMPLE IX

Four grams of the $NH_4$ Zeolon 500, as prepared in Example VIII, diluted with 4 g quartz chips, was packed into a quartz reactor and calcined at 500° C. for 16 hours with air. Aqueous methanol of 30% by weight was fed through the catalyst bed at 450° C. at total WHSV of 1.1. The results of methanol conversion and product selectivities at 5 minutes and 60 minutes on stream are summarized in Table VI.

TABLE VI
Methanol Conversion Over Zeolon 500 with Water Diluent

| Stream (minutes) | Conversion to Hydrocarbons | Product Selectivity | | | | Others |
|---|---|---|---|---|---|---|
| | | $C_2H_4$ | $C_3H_6$ | $C_4H_8$ | $C_1°-C_4°$ | |
| 5 | 77.2 | 54.4 | 15.7 | 4.2 | 23.4 | 2.3 |
| 60 | 40.3 | 29.4 | 17.7 | 18.7 | 30.9 | 3.3 |

The Table VI data indicate that the catalyst aged to less than 50% conversion within 60 minutes with water as diluent.

EXAMPLE X

Two grams of NH$_4$ zeolon 500 catalyst, prepared in Example VIII, was diluted with 4 grams of quartz chips and packed into a stainless steel metal reactor. The catalyst was flushed with H$_2$ at 400° C., 125 psi and 100 cc/min. for 16 hours. After methanol and hydrogen were on stream for 30 hours, the reaction conditions were adjusted to 415° C., 250 psi, H$_2$ feed at 100 cc/min, MeOH feed at 1 cc/hr. Methanol conversion results are shown in Table VII.

TABLE VII

Methanol Conversion Over Zeolon 500 With Hydrogen Diluent

| Time on Stream (Hours) | MeOH Conversion to Hydrocarbons | Product Selectivity C$_2$H$_4$-C$_4$H$_8$ |
|---|---|---|
| 2 | 63 | 58 |
| 4 | 63 | 57 |
| 6 | 62 | 57 |
| 8 | 62 | 58 |
| 8.7 | 61 | 56 |

The Table VII data indicate that under the Example X conditions, the catalyst maintained methanol conversion higher than 60% for at least 8.7 hours. The major products are ethylene, propylene and butenes. As compared to results shown in Example IX, the catalyst lifetime is significantly prolonged by addition of hydrogen.

What is claimed is:

1. In a catalytic process for converting a feedstock comprising the organic reactants methanol, methyl ether or mixtures thereof to a hydrocarbon product rich in ethylene and propylene, which process comprises contacting said feedstock under conversion conditions including a temperature between about 200° C. and 500° C. and a weight hourly space velocity for the organic reactants of between about 0.05 and 30, in a reaction zone with a catalyst comprising a crystalline aluminosilicate zeolite material characterized by a crystalline structure having pore windows formed by 8-membered rings of oxygen atoms, the improvement for enhancing catalyst lifetime comprising:
   (i) simultaneously co-feeding to said reaction zone a catalyst lifetime enhancing amount of a gaseous elemental hydrogen-containing diluent, said diluent being co-fed into said reaction zone at a weight hourly space velocity of from about 0.003 to 20; and
   (ii) maintaining said feedstock at a pressure between about 50 and 500 psig.

2. A process according to claim 1 wherein said zeolite material is selected from erionite, offretite, chabazite, chabazite-erionite combinations, Zeolite T, Zeolite W and ZSM-34.

3. A process according to claim 2 wherein the conversion conditions include a temperature of from about 300° C. to 450° C., and reaction zone pressure from about 100 psig to 250 psig.

4. A process according to claim 3 wherein said zeolite is ZSM-34.

5. A process according to claim 4, wherein said gaseous diluent is elemental hydrogen.

6. A process according to claim 3 wherein the weight hourly space velocity of the elemental hydrogen ranges from about 0.01 to 10 and the molar ratio of elemental hydrogen to organic reactants ranges from about 0.5:1 to 40:1.

7. A process according to claim 6 wherein said feedstock also comprises water present in an amount of at least about 0.25 moles of water per mole of organic reactants.

8. A process according to claim 3 wherein said gaseous diluent comprises a mixture of elemental hydrogen and carbon monoxide in an elemental hydrogen to carbon monoxide molar ratio of from about 0.2:1 to 10:1.

9. A process according to claim 8 wherein said gaseous diluent comprises synthesis gas derived from gasification of fossil fuel.

10. A process according to claim 8 wherein said feedstock also comprises water present in an amount of at least 0.25 moles of water per mole of organic reactants.

11. A process according to claim 1 wherein said catalyst further comprises a binder for said zeolite material.

12. In a catalytic process for converting a methanol-containing feedstock to a hydrocarbon product rich in ethylene and propylene, which process comprises contacting said feedstock under conversion conditions including a temperature between about 200° C. and 500° C. and a weight hourly space velocity for the methanol of between about 0.05 and 30, in a reaction zone with a catalyst comprising the crystalline zeolite material ZSM-34, the improvement for enhancing catalyst lifetime comprising:
   (i) simultaneously co-feeding to said reaction zone at a weight hourly space velocity of from about 0.003 to 20 a catalyst lifetime enhancing amount of an elemental hydrogen diluent; and
   (ii) maintaining said feedstock at a pressure between about 50 and 500 psig.

13. A process according to claim 12 wherein the conversion conditions include a temperature of from about 300° C. to 450° C., and a reaction zone pressure from about 100 psig to 250 psig.

14. A process according to claim 12 wherein the weight hourly space velocity of the elemental hydrogen ranges from about 0.01 to 10 and the molar ratio of elemental hydrogen to methanol ranges from about 0.5:1 to 40:1.

15. A process according to claim 12 wherein said zeolite material is used in its ammonium-exchanged form.

16. In a catalytic process for converting a methanol-containing feedstock to a hydrocarbon product rich in ethylene and propylene, which process comprises contacting said feedstock under conversion conditions including a temperature between about 200° C. and 500° C. and a weight hourly space velocity for the organic reactants of between about 0.05 and 30, in a reaction zone with a catalyst comprising a natural crystalline zeolite material which is a combination of chabazite and erionite, the improvement of enhancing catalyst lifetime comprising:
   (i) simultaneously co-feeding to said reaction zone at a weight hourly space velocity of from about 0.003 to 20 a catalyst lifetime enhancing amount of an elemental hydrogen diluent; and
   (ii) maintaining said feedstock at a pressure between about 50 and 500 psig.

17. A process according to claim 16 wherein the conversion conditions include a temperature of from about 300° C. to 450° C., and a reaction zone pressure from about 100 psig to 250 psig.

18. A process according to claim 16 wherein the weight hourly space velocity of the elemental hydrogen to organic reactants ranges from about 0.5:1 to 40:1.

19. A process according to claim 16 wherein the zeolite material is used in its ammonium-exchanged form.

20. A process according to claim 16 wherein said zeolite material is Zeolon 500.

* * * * *